United States Patent [19]

Quinlan

[11] 4,264,767
[45] Apr. 28, 1981

[54] α-1,4-THIAZINE ALKANEPHOSPHONIC ACIDS

[75] Inventor: Patrick M. Quinlan, Webster Groves, Mo.

[73] Assignee: Petrolite Corporation, St. Louis, Mo.

[21] Appl. No.: 932,257

[22] Filed: Aug. 9, 1978

[51] Int. Cl.$^3$ .................................. C07D 279/10
[52] U.S. Cl. ............................................. 544/57
[58] Field of Search ................................... 544/57

[56] References Cited

U.S. PATENT DOCUMENTS

| | | | |
|---|---|---|---|
| 2,706,194 | 4/1955 | Morris et al. | 544/57 |
| 3,359,266 | 12/1967 | Maier | 544/57 |
| 3,539,561 | 11/1970 | Budde et al. | 544/57 |
| 3,652,742 | 3/1972 | Sirrenberg et al. | 544/57 |
| 3,658,800 | 4/1972 | Beriger | 544/57 |

OTHER PUBLICATIONS

Karrer, Organic Chemistry, 2nd Ed. Elsevier Pub. Co. (N.Y.) 1946, pp. 901–902.

*Primary Examiner*—John M. Ford
*Attorney, Agent, or Firm*—Sidney B. Ring; Hyman F. Glass

[57] ABSTRACT

This invention relates to α-1,4-thiazine alkanephosphonic acids; and to the preparation and uses thereof.

8 Claims, No Drawings

α-1,4-THIAZINE ALKANEPHOSPHONIC ACIDS

This invention relates to novel α-1,4-thiazine alkanephosphonic acids of the formula:

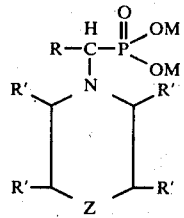

where R is a substituted group, for example, a hydrocarbon or a substituted hydrocarbon group such as alkyl, cycloalkyl, alkenyl, aryl, aralkyl, substituted aryl, ect.; R' is hydrogen or a substituted group, such as a hydrocarbon group, such as alkyl, etc.; Z is S,

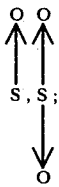

and M is hydrogen or a salt moiety for example an alkali metal, alkaline earth metal, alkyl ammonium, ammonium, etc.; and to uses thereof.

It has been shown by A. Ford—Moore, *J. Chem. Soc.* 1949, p. 2433, when divinyl sulfone is treated with primary amines, derivatives of 1,4-thiazine-1,1-dioxide result. In the present invention I have reacted an α-aminoalkanephosphonic acid with an equal molar amount of a divinyl sulfur compound to produce the novel α-1,4-thiazine alkanephosphonic acids. The reaction may be summarized by the following equation:

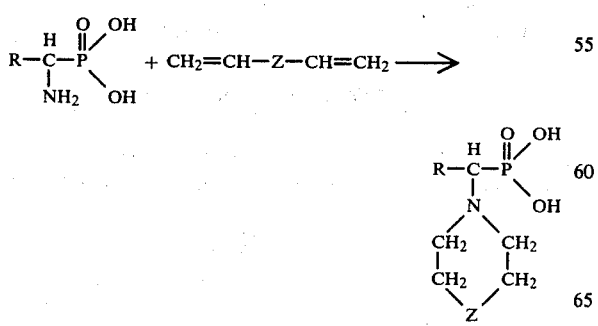

Examples of the divinyl sulfur compounds are:

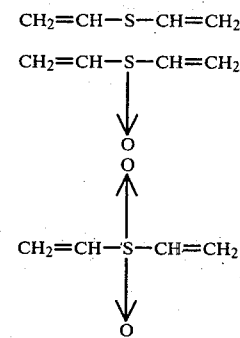

The α-aminoalkanephosphonic acids were synthesized by several methods that have been described by R. Tyka, *Tetrahedron Lett.* 1970, p. 677., J. Lukszo, R. Tyka, *Synthesis* 1977, p. 239, and R. Gancarz, *Synthesis* 1977, p. 635.

In carrying out the reaction it is preferred to carry out the reaction in a solvent or a mixture of solvents in which the α-amino phosphonic acid is soluble. To the solution of the α-amino phosphonic acid in a suitable solvent or mixture of solvents is slowly added the divinyl sulfone. The preferred temperature is about 20° to 50° C. though higher or lower temperatures may be employed. A catalyst such as triethylamine may be used. In most instances, upon cooling, the α-1,4-thiazine alkanephosphonic acid precipitates and is purified by recrystallization. In some cases it is necessary to reduce the final volume in order to isolate the desired product.

These products have a wide variety of uses such as in acid corrosion inhibitors, scale inhibitors, chelating agents, microbiocides, etc.

The invention may be illustrated by the following examples.

EXAMPLE 1

To a solution of α-aminoethylphosphonic acid 12.6 g. (0.1 mol) in 50 ml. of a 50:50 (by volume) mixture of ethanol and water was slowly added, with stirring, divinyl sulfone 11.8 g. (0.1 mol). The reaction mixture became warm and upon cooling deposited crystals. After cooling in an ice bath, the crystalline product was filtered and washed with cold ethanol. The product was recrystallized from aqueous ethanol. The product had the following structure which was characterized by H' and $P^{31}$ NMR spectrum.

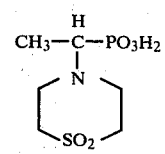

Anal. Calcd. for $C_6H_{14}O_5NPS$: P, 12.70; N, 5.74; S, 13.11; Found: P, 12.59; N, 5.68; S, 13.21.

EXAMPLE 2

To a solution of α-aminopropylphosphonic acid 13.9 g. (0.1 mol) in 50 ml. of aqueous ethanol was slowly added, with stirring, divinyl sulfone 11.8 g. (0.1 mol). The reaction mixture became warm and deposited crystals upon cooling. The product was filtered and washed with cold ethanol. It was recrystallized from aqueous ethanol. It had the following structure.

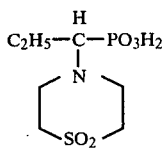

Anal. Calcd. for $C_7H_{16}O_5NPS$: P, 12.06; N, 5.45; S, 12.45; Found: P, 12.00; N, 5.38; S, 12.33.

EXAMPLE 3

In a similar manner α-aminobenzylphosphonic acid 18.7 g. (0.1 mol) was reacted with divinyl sulfone 11.8 g. (0.1 mol). The product was found to have the following structure:

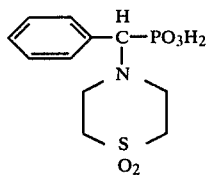

Anal. Calcd. for $C_{11}H_{16}O_5NPS$: P, 10.16; N, 4.59; S, 10.49. Found: P, 10.24; N, 4.61; S, 10.65.

To avoid repetitive detail, the following table was constructed to further illustrate examples of this invention that were prepared in a similar manner.

$$R-\underset{\underset{N}{|}}{\overset{\overset{H}{|}}{C}}-PO_3H_2$$
(with N in a ring containing SO$_2$)

| | R | | R |
|---|---|---|---|
| Ex. 4 | $C_3H_7$ | Ex. 8 | $C_6H_{13}$ |
| Ex. 5 | $C_6H_5CH_2$ | Ex. 9 | $C_{11}H_{23}$ |
| Ex. 6 | HO—C$_6$H$_4$— | Ex. 10 | $C_{17}H_{33}$ |
| Ex. 7 | H$_3$C—C$_6$H$_4$— | Ex. 11 | $C_{17}H_{35}$ |

USE AS A SCALE INHIBITOR

Scale formation from aqueous solutions containing an oxide variety of scale forming compounds, such as calcium, barium and magnesium carbonate, sulfate, silicate, oxalates, phosphates, hydroxides, fluorides and the like are inhibited by the use of threshold amounts of the compositions of this invention which are effective in small amounts, such as less than 2.5 p.p.m.

The compounds of the present invention (i.e., the acid form of the compounds) may be readily converted into the corresponding alkali metal, ammonium or alkaline earth metal salts by replacing at least half of the hydrogen ions in the phosphonic acid group with the appropriate ions, such as the potassium ion or ammonium or with alkaline earth metal ions which may be converted into the corresponding sodium salt by the addition of sodium hydroxide. If the pH of the amine compound is adjusted to 7.0 by the addition of caustic soda, about one half of the—OH radicals on the phosphorous atoms will be converted into the sodium salt form.

The scale inhibitors of the present invention illustrate improved inhibiting effect at high temperatures when compared to prior art compounds. The compounds of the present invention will inhibit the deposition of scale-forming alkaline earth metal compounds on a surface in contact with aqueous solution of the alkaline earth metal compounds over a wide temperature range. Generally, the temperatures of the aqueous solution will be at least 40° F., although significantly lower temperatures will often be encountered. The preferred temperature range for inhibition of scale deposition is from about 130° to about 350° F. The aqueous solutions or brines requiring treatment generally contain about 50 p.p.m. to about 50,000 p.p.m. of scale-forming salts. The compounds of the present invention effectively inhibit scale formation when present in an amount of from 0.1 to about 100 p.p.m., and preferably 0.2 to 50 p.p.m. wherein the amounts of the inhibitor are based upon the total aqueous system. There does not appear to be a concentration below which the compounds of the present invention are totally ineffective. A very small amount of the scale inhibitor is effective to a correspondingly limited degree, and the threshold effect is obtained with less than 0.1 p.p.m. There is no reason to believe that this is the minimum effective concentration. The scale inhibitors of the present invention are effective in both brine, such as sea water, and acid solutions.

The following examples are presented to illustrate the use of the phosphonates prescribed herein and are presented for purposes of illustration and not of limitation.

The following test was used to evaluate these compositions as scale inhibitors.

Procedure:
1. Make up stock $CaCl_2.2H_2O$, 2.94 g/L or 56 g/5 gallons (18.9 liters)
2. Stock $NaHCO_3$ should be 3.35 g/L or 64 g/5 gallons.
3. Inhibitors—Make 0.1 percent solutions in deionized water. 1 ml in 100 sample=10 p.p.m. (Test at 5, 20, and 50 p.p.m.).

Put 50 ml bicarbonate solution into 100 ml milk dilution bottle. Add inhibitor (for 100 ml final volume). Then add 50 ml CaCl$_2$ solution and set in bath at 180° F. Do not cap. Always prepare a blank. Run a hardness determination on a 50—50 mixture before heating.

Heat at 180° F. Take 10 ml samples from bottles after 2 hours and 4 hours.

Filter through millipore filter.
Run total hardness on filtrate.
Calculate as % Ca still in solution, i.e., $$\frac{\text{Total hardness after heating}}{\text{Total hardness before heating}} \times 100 = \%$$

The compounds were tested at 180° F. at the concentration shown. Readings were taken after 2 and 4 hours.

TABLE A

| | Scale Inhibitor Tests | |
|---|---|---|
| Compound | Concentration | % Protection |
| Example 1 | 5 p.p.m. | 25 |
| | 50 p.p.m. | 45 |

TABLE A-continued

Scale Inhibitor Tests

| Compound | Concentration | % Protection |
|---|---|---|
| Example 1 (sodium salt) | 50 p.p.m. | 44 |
| Example 2 | 5 p.p.m. | 30 |
| Example 2 (sodium salt) | 5 p.p.m. | 31 |
| Example 3 (sodium salt) | 5 p.p.m. | 25 |
|  | 50 p.p.m. | 42 |
| Example 4 (sodium salt) | 5 p.p.m. | 24 |
|  | 50 p.p.m. | 43 |
| Typical Commercial Inhibitor | 5 p.p.m. | 24% |
|  | 50 p.p.m. | 30% |

USE IN ACID SYSTEMS

The compounds of this invention can also be employed as corrosion inhibitors for acid systems, for example as illustrated by the pickling of ferrous metals, the treatment of calcareous earth formations, etc., as described in the following sections.

USES

This invention also relates to the inhibition of corrosion, particularly the corrosion of metals in contact with the acid solutions.

The present invention is especially useful in the acidizing or treating of earth formations and wells traversed by a bore hole. It may also be used in metal cleaning and pickling baths which generally comprise aqueous solutions of inorganic acids such as sulfuric acid, hydrochloric acid, phosphoric acid and are useful in the cleaning and treatment of iron, zinc, ferrous alloys, and the like.

If no corrosion inhibitor is present when the aqueous acidic solution comes in contact with the metal, excessive metal loss and consumption or loss of acid, and other adverse results will be experienced. There has been a continuing search for corrosion inhibitors which can be used effectively in small concentrations, and which are economical to produce. The need is also for corrosion inhibitors which are effective at high temperatures, e.g., 200° F. and above, such as are found in operations involving acidic solutions, particularly oil-well acidizing where higher and higher temperatures are found as the well extends further into the earth.

While the compounds of this invention are of themselves particularly good acid corrosion inhibitors, optionally they may be blended with acetylenic alcohols, dispersing and solubilizing agents such as ethoxylated phenols, alcohols, and fatty acids. They may also be blended with such known acid inhibitors as the quinoline or alkyl pyridine quaternary compounds or synergists such as terpene alcohols, formamide, formic acid, alkyl amine, alkylene polyamines, heterocyclic amines, and the like.

Quaternary ammonium compounds may be illustrated by C-alkyl pyridine-N-methyl chloride quaternary, C-alkyl pyridine-N-benzyl chloride quaternary, quinoline-N-benzyl chloride quaternary, isoquinoline-N-benzyl chloride quaternary, thioalkyl pyridine quaternaries, thioquinoline quaternaries, benzoquinoline quaternaries, thiobenzoquinoline quaternaries, imidasole quaternaries, pyrimidine quaternaries, carbazole quaternaries, the corresponding ammonium compounds, pyridines and quinolines may also be used alone or in combination with the quaternary compounds. Thus a pyridine plus quinoline quaternary, a quinoline plus quinoline quaternary, or quinoline or amine alone or in combination may be used.

The formic acid compound may be selected from the esters and amides of formic acid. The formic acid compound may be from the group consisting of formate esters of the structure:

HCOOR where R is a monoaryl group, an alkyl group having 1 to 6 carbon atoms, cyclo-alkyl residues having 5 to 6 carbon atoms, alkenyl and alkynl groups having 2 to 6 carbon atoms which may contain functional groupings selected from —C—OH, —OH, =C=O, —COOH, —SH, and $NH_2$. Examples of the formic acid compound are: methyl formate, ethyl formate, benzyl formate, other alkyl and aryl formates, and the like. Other examples include formamide, dimethyl formamide, formanilide, and the like. Mixtures of the esters and mixtures of the amides may be used.

USE IN ACIDIZING EARTH FORMATIONS

The compositions of this invention can also be used as corrosion inhibitors in acidizing media employed in the treatment of deep wells to reverse the production of petroleum or gas therefrom and more particularly to an improved method of acidizing a calcareous or magnesium oil-bearing formation.

It is well known that production of petroleum or gas from a limestone, dolomite, or other calcareous-magnesian formation can be stimulated by introducing an acid into the producing well and forcing it into the oil or gas bearing formation. The treating acid, commonly a mineral acid such as HCl, is capable of forming water soluble salts upon contact with the formation and is effective to increase the permeability thereof and augment the flow of petroleum to the producing well.

Corrosion Test Procedure

In these tests the acid solutions were mixed by diluting concentrated hydrochloric acid with water to the desired concentrations.

Corrosion coupons of 1020 steel (AISI) were pickled in an uninhibited 10% HCl solution for 10 minutes, neutralized in a 10% solution of $NaHCO_3$, dipped in acetone to remove water and allowed to dry. They were then weighed to the nearest milligram and stored in a desicator.

In most of the tests, a 25 cc/in$^2$ acid volume to coupon surface area ratio was used. After the desired amount of acid was poured into glass bottles, the inhibitor was added. The inhibited acid solution was then placed in a water bath which had been set at a predetermined temperature and allowed to preheat for 20 minutes. After which time, the coupons were placed in the preheated inhibited acid solutions. The coupons were left in the acid solutions for the specified test time, then removed, neutralized, recleaned, rinsed, dipped in acetone, allowed to dry, then reweighed.

The loss in weight in grams was multiplied times a calculated factor to convert the loss in weight to lbs./ft$^2$/24 hours. The factor was calculated as follows:

$$\frac{\frac{144 \text{ in}^2}{\text{ft}^2}}{\frac{454 \text{ g}}{\text{lb}} \times \text{Surface Area of Coupon (in}^2) \times \frac{1 \text{ day}}{24 \text{ hrs.}}} = \text{Factor}$$

| CORROSION INHIBITION IN 15% HCl | | | | |
|---|---|---|---|---|
| Inhibitor | p.p.m. | Test Temp. | Test Time | Corrosion Rate (lbs/ft$^2$/day) |
| Ex. 3 | 2000 | 150° F. | 4 hrs. | 0.075 |
| Ex. 5 | 2000 | 150° F. | 4 hrs. | 0.065 |
| Ex. 8 | 2000 | 150° F. | 4 hrs. | 0.062 |
| Ex. 9 | 2000 | 150° F. | 4 hrs. | 0.042 |
| Ex. 10 | 2000 | 150° F. | 4 hrs. | 0.035 |
| Blank | 2000 | 150° F. | 4 hrs. | 0.290 |

USE AS A MICROBIOCIDE

(I) In water treatment

This phase of the present invention relates to the treatment of water. More particularly, it is directed to providing improved means for controlling microbiological organisms including bacteria, fungi, algae, protozoa, and the like, present in water.

It is well known that ordinary water contains various bacteria, fungi, algae, protozoa and other microbiological organisms which, if uncontrolled, multiply under certain conditions so as to prevent many serious problems. For example, in swimming pools the growth of these microbiological organisms is very undesirable from a sanitary standpoint as well as for general appearances and maintenance. In industrial water systems such as cooling towers, condenser boxes, spray condensers, water tanks, basins, gravel water filters, and the like, microbiological organisms may interfere greatly with proper functioning of equipment and result in poor heat transfer, clogging of systems and rotting of wooden equipment, as well as many other costly and deleterious effects.

In other industrial applications where water is used in processes, as for example, as a carrying medium, etc., microbiological organisms may also constitute a problem in maintenance and operation. Illustrative of such industrial applications are the pulp and paper manufacturing processes, oil well flooding operations and the like.

The products of this invention are suitable as biocides for industrial, agricultural and horticultural, military, hygienic and recreational water supplies. They provide an inexpensive, easily prepared group of products which can be used, in minimal amounts, in water supplies, in cooling towers, air-conditioning systems, on the farm and ranch, in the factory, in civilian and military hospitals and dispensaries, in camps, for swimming pools, baths and aquaria, waterworks, wells, reservoirs, by fire-fighting agencies, on maritime and naval vessels, in boilers, steam-generators and locomotives, in pulp and paper mills, for irrigation and drainage, for sewage and waste disposal, in the textile industry, in the chemical industries, in the tanning industry, et cetera, and which will render said water supplies bactericidal, fungicidal and algicidal. They further provide a simple process whereby water supplies, for whatever purposes intended, are rendered bacteriostatic, fungistatic and algistatic, i.e., said water supplies treated by the process of this invention will resist and inhibit the further growth or proliferation of bacteria, fungi, algae and all forms of microbial life therein.

(II) Water flooding in secondary recovery of oil

This phase of the present invention relates to secondary recovery of oil by water flooding operations and is more particularly concerned with an improved process for treating flood water and oil recovery therewith. More particularly this invention relates to a process of inhibiting bacterial growth in the recovery of oil from oil-bearing strata by means of water flooding taking place in the presence of sulfate-reducing bacteria.

Water flooding is widely used in the petroleum industry to effect secondary recovery of oil. By employing this process the yield of oil from a given field may be increased beyond the 20–30 percent of the oil in a producing formation that is usually recovered in the primary process. In flooding operation, water is forced under pressure through injection wells into or under oil-bearing formations to displace the oil therefrom to adjacent producing wells. The oil-water mixture is usually pumped from the producing wells into a receiving tank where the water, separated from the oil, is siphoned off, and the oil then transferred to storage tanks. It is desirable in carrying out this process to maintain a high rate of water injection with a minimum expenditure of energy. Any impediment to the free entry of water into oil bearing formations seriously reduces the efficiency of the recovery operation.

The term "flood water" as herein employed is any water injected into oil bearing formations for the secondary recovery of oil. In conventional operations, the water employed varies from relatively pure spring water to brine and is inclusive of water reclaimed from secondary recovery operations and processed for recycling. The problems arising from the water employed depend in part on the water used. However, particularly troublesome and common to all types of water are problems directly or indirectly concerned with the presence of microorganisms, such as bacteria, fungi and algae. Microorganisms may impede the free entry of water into oil-bearing formations by producing ions susceptible of forming precipitates, forming slime and/or existing in sufficiently high numbers to constitute an appreciable mass, thereby plugging the pores of the oil-bearing formation. Free plugging increases the pressure necessary to drive a given volume of water into an oil-bearing formation and oftentimes causes the flooding water to by-pass the formation to be flooded. In addition, microorganisms may bring about corrosion by acting on the metal structures of the wells involved, producing corrosive substances such as hydrogen sulfide, or producing conditions favorable to destructive corrosion such as decreasing the pH or producing oxygen. The products formed as the result of corrosive action may also be pore-plugging precipitates. Usually, the difficulties encountered are a combination of effects resulting from the activity of different microorganisms.

(III) Hydrocarbon treatment

This phase of the present invention relates to the use of these compounds as biocides in hydrocarbon systems.

In addition to being used as biocides in aqueous systems, the compounds of this invention can also be employed as biocides in hydrocarbon systems, particularly when petroleum products are stored. It is believed that bacteria and other organisms, which are introduced into hydrocarbon systems by water, feed readily on hydrocarbons resulting in a loss in product; that microorganisms cause the formation of gums, H₂S, peroxides, acids and slimes at the interface between water and oil; that bacterial action is often more pronounced with rolling motion than under static conditions, etc. Loss of product, corrosion of the storage tank, clogging of filters and metering instruments, and fuel deterioration are among the harmful effects of bacteria growth in fuels. The activity of microorganism growth is often increased by the presence of rust. Not only do these microorganisms often encourage rust but rust encourages microorganism growth. Since microorganism growth appears to be considerably higher with kerosene than with gasoline, plugged filters experienced with jet fuels which contain large amounts of kerosene is a serious problem.

The compositions of this invention can be employed in hydrocarbon systems.

MICROBIOCIDAL TESTING

The screening procedure was as follows: a one percent by weight solution of the test compound in water was prepared. The solution was aseptically added to a sterile broth that would support the growth of the test organism, *Desulfovibro desulfuricans*, to provide the specified concentration given by weight of test compound per million parts by weight of broth. A general growth medium, such as prescribed by the American Petroleum Institute was used. The broth containing the test compound then was dispersed in 5 cc. amounts into sterile disposable tubes and the tubes were inoculated with the growing test organism and incubated at 35° C. for 24 hours. The absence or presence of growth of the microorganisms was determined by visual inspection by an experienced observer.

Following is a summary of the results of the testing of examples of this invention.

| Compound Example Number | Concentration in p.p.m. | Results |
|---|---|---|
| 3 (Sodium salt) | 75 | gave control |
| 9 (sodium salt) | 25 | gave control |
| 10 (sodium salt) | 50 | gave control |

*By control is meant that the test compound was biostatic or biocidal - i.e., no growth of the test organism occurred under the test conditions.

I claim:

1. A compound of the formula

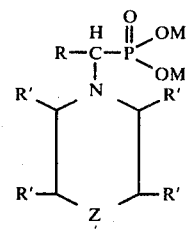

where R is a member of the group selected from the group consisting of alkyl, alkenyl, cycloalkyl, aryl, alkaryl, aralkyl, and hydroxyphenyl, and R' is hydrogen or alkyl, Z is S, SO, or SO₂ and M is a hydrogen or a salt moiety.

2. The compound of claim 1 where R' is a hydrogen and Z is SO₂.

3. The compound of claim 1 where R is methyl, ethyl, propyl, hexyl, undecyl, heptadecenyl, heptadecyl, phenyl, hydroxyphenyl, tolyl, benzyl, or cyclohexyl.

4. The compound of claim 1 where R is —CH₃, Z is SO₂ and M is H.

5. The compound of claim 1 where R is

Z is SO₂ and M is H.

6. The compound of claim 1 where R is

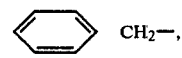

Z is SO₂ and M is H.

7. The compound of claim 1 where R is H₃C

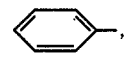

Z is SO₂ and M is H.

8. The compound of claim 1 where R is C₁₇H₃₃—, Z is SO₂ and M is H.

* * * * *